US 8,941,739 B2

(12) United States Patent
Yoo

(10) Patent No.: US 8,941,739 B2
(45) Date of Patent: Jan. 27, 2015

(54) APPARATUS AND METHOD FOR DETECTING ROAD SURFACE PROPERTIES

(75) Inventor: Hyun Jae Yoo, Gyeonggi-do (KR)

(73) Assignee: Hyundai Motor Company, Seoul (KR)

( * ) Notice: Subject to any disclaimer, the term of this patent is extended or adjusted under 35 U.S.C. 154(b) by 394 days.

(21) Appl. No.: 13/432,527

(22) Filed: Mar. 28, 2012

(65) Prior Publication Data

US 2013/0141577 A1 Jun. 6, 2013

(30) Foreign Application Priority Data

Dec. 1, 2011 (KR) ........................ 10-2011-0127752

(51) Int. Cl.
*H04N 7/18* (2006.01)
*G06F 7/00* (2006.01)
*G01S 17/88* (2006.01)

(52) U.S. Cl.
CPC ..................................... *G01S 17/88* (2013.01)
USPC ............ 348/148; 356/4.01; 356/601; 701/36; 348/222

(58) Field of Classification Search
USPC ................................................... 348/41–161
See application file for complete search history.

(56) References Cited

U.S. PATENT DOCUMENTS

| 4,781,465 | A | * | 11/1988 | Demachi et al. | ............... 356/602 |
| 4,796,998 | A | * | 1/1989 | Soma et al. | ................... 356/608 |
| 6,059,686 | A | * | 5/2000 | Takahashi | ....................... 477/47 |
| 6,452,684 | B1 | * | 9/2002 | Mennink | ....................... 356/601 |
| 6,810,330 | B2 | * | 10/2004 | Matsuura | ...................... 701/301 |
| 6,965,438 | B2 | * | 11/2005 | Lee et al. | ....................... 356/625 |
| 7,274,436 | B2 | * | 9/2007 | Matsuura et al. | ............. 356/4.01 |
| 7,973,911 | B2 | * | 7/2011 | Takahashi | ...................... 356/4.01 |
| 8,126,625 | B2 | * | 2/2012 | Makino et al. | .................. 701/65 |
| 8,229,664 | B2 | * | 7/2012 | Herbert et al. | ................. 701/301 |
| 2006/0060441 | A1 | * | 3/2006 | Sakai et al. | ....................... 191/2 |
| 2008/0129541 | A1 | * | 6/2008 | Lu et al. | ........................ 340/905 |
| 2009/0015683 | A1 | * | 1/2009 | Ando | .......................... 348/222.1 |
| 2012/0001769 | A1 | * | 1/2012 | Nitanda et al. | ................. 340/901 |
| 2012/0203428 | A1 | * | 8/2012 | Choi et al. | ....................... 701/37 |

FOREIGN PATENT DOCUMENTS

| JP | 08-193944 | 7/1996 |
| JP | 2002039861 A | 2/2002 |
| JP | 2006-046936 A | 2/2006 |
| JP | 2010-164521 A | 7/2010 |
| KR | 10-2010-0122149 | 11/2010 |
| KR | 10-2011-0061741 | 6/2011 |

* cited by examiner

*Primary Examiner* — Joseph Ustaris
*Assistant Examiner* — Talha Nawaz
(74) *Attorney, Agent, or Firm* — Edwards Wildman Palmer LLP; Peter F. Corless

(57) ABSTRACT

Disclosed is a technique for detecting a road surface property. More specifically, the technique includes a reflectivity table that stores a degree of reflectivity of a rainy road relative to a reference reflectivity and a degree of reflectivity of a snowy road relative to the reference reflectivity. A reflection measurement unit measures a reflection which is the amount of a laser beam that is emitted through a light emitting unit of a laser sensor, reflected from the road surface, and received by a light receiving unit, and a reflectivity calculation unit calculates a degree of reflectivity for the road in front of the vehicle via a ratio of the measured reflection and the reference reflectivity. A road surface property determination unit then detects the corresponding road surface property based on the reflectivity table.

8 Claims, 5 Drawing Sheets

APPARATUS AND METHOD FOR DETECTING ROAD SURFACE PROPERTIES

CROSS-REFERENCES TO RELATED APPLICATIONS

Priority to Korean patent application number 10-2011-0127752, filed on Dec. 1, 2011, which is incorporated by reference in its entirety, is claimed.

BACKGROUND OF THE INVENTION

1. Field of the Invention

The present invention relates to an apparatus and a method for detecting one or more road surface properties, and more particularly, to an apparatus and a method for detecting the condition of a road surface (e.g., the degree of geometric irregularity) as well as the associated properties of the road thereof (e.g., rainy snowy or icy conditions) by using a single laser sensor mounted on a front portion of a vehicle.

2. Description of the Related Art

As vehicles become more and more advanced, manufacturers have begun to provide a higher degree of technology equipment to aide the driver in operating vehicles in a safe manner. Although there are currently sensors and monitoring devices detect and monitor other vehicles on the road, vehicle manufactures have yet to develop an effective technique for detecting road conditions (such as irregularities in the road, snow, ice, rain, etc.).

The conventional technique utilizes a single laser sensor to determine whether there is a bump or recess in the upcoming road. The single laser sensor measures the time it takes for a projected laser beam to travel from the sensor and back from the road surface. This data is then used to provide additional control to vehicle to prevent accidents and damage to the car. However, this conventional technology cannot detect the road properties or conditions, such as snow, ice, rain, etc., which for the most part are even more dangerous than a bump or recess in the road. Thus, there is a need for a technology that can effectively determine the conditions of the road the vehicle is currently travelling on and provide additional control to the vehicle accordingly.

SUMMARY OF THE INVENTION

Accordingly, the present invention has been made in view of the above problems. More specifically, the present invention provides an apparatus and a method for detecting at least one road surface property. A road surface may be defined as wet conditions, snowy conditions, or icy conditions etc. Road surface properties are detected by measuring a rate of reflection (reflectivity) at which a laser beam is bounced back by using a single laser sensor mounted on a front portion of a vehicle.

According to an aspect of the present invention, an apparatus for detecting a property of a road surface includes: a reflectivity table configured to store a degree of reflectivity of a rainy road relative to a reference reflectivity and a degree of reflectivity of a snowy road relative to the reference reflectivity; a reflection measurement unit configured to measure a reflection rate which is an amount of a laser beam that is emitted through a light emitting unit of a laser sensor, reflected from the road surface, and received by a light receiving unit; a reflectivity calculation unit configured to calculate a degree of reflectivity (i.e., a ratio of the reflection measured by the reflection measurement unit to the reference reflectivity); and a road surface property determination unit configured to determine at least one road surface property corresponding to the degree of reflectivity calculated by the reflectivity calculation unit based on the reflectivity table.

According to another aspect of the present invention, an apparatus for detecting a property of a road surface includes: a reflectivity table configured to store a degree of reflectivity of a rainy road relative to a reference reflectivity and a degree of reflectivity of a snowy road relative to the reference reflectivity; an image processing unit configured to detect abnormality of the road surface based on a road surface image of a road in front of a vehicle captured by a image capturing device; a driving control unit configured to operate a laser sensor upon detection of the abnormality of the road surface by the image processing unit; a reflection measurement unit configured to measure a reflection (i.e., an amount of a laser beam that is emitted through a light emitting unit of the laser sensor, reflected from the road surface, and received by a light receiving unit); a reflectivity calculation unit configured to calculate a degree of reflectivity (i.e., a ratio of the reflection measured by the reflection measurement unit to the reference reflectivity); and a road surface property determination unit configured to determine the property of the road surface corresponding to the degree of reflectivity calculated by the reflectivity calculation unit based on the reflectivity table.

According to another aspect of the present invention, a method of detecting a property of a road surface includes: providing a reflectivity table configured to store a degree of reflectivity of a rainy road relative to a reference reflectivity and a degree of reflectivity of a snowy road relative to the reference reflectivity; measuring, by a reflection measurement unit, a reflection (i.e., an amount of a laser beam that is emitted through a light emitting unit of a laser sensor, reflected from the road surface, and received by a light receiving unit); calculating, by a reflectivity calculation unit, a degree of reflectivity by calculating a ratio of the reflection which is measured by the reflection measurement unit to the reference reflectivity; and determining, by a road surface property determination unit, the at least one road surface property corresponding to the degree of reflectivity calculated by the reflectivity calculation unit based on the reflectivity table.

According to another aspect of the present invention, a method of detecting a property of a road surface includes: providing a reflectivity table configured to store a degree of reflectivity of a rainy road relative to a reference reflectivity and a degree of reflectivity of a snowy road relative to the reference reflectivity; detecting, by an image processing unit, abnormalities on the road surface based on a surface image of the road in front of a vehicle captured by a image capturing device; operating, by a control unit, a laser sensor upon detection of the abnormality on the road surface by the image processing unit; measuring, by a reflection measurement unit, a reflection which is an amount of a laser beam that is emitted through a light emitting unit of the laser sensor, reflected from the road surface, and received by a light receiving unit; calculating, by a reflectivity calculation unit, a degree of reflectivity which is a ratio of the reflection measured by the reflection measurement unit to the reference reflectivity; and determining, by a road surface property determination unit, at least one road surface property corresponding to the degree of reflectivity calculated by the reflectivity calculation unit based on the reflectivity table.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION OF THE INVENTION

Exemplary embodiments of the present invention will be described herein below with reference to the accompanying drawings.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, combustion, plug-in hybrid electric vehicles, hydrogen-powered vehicles and other alternative fuel vehicles (e.g. fuels derived from resources other than petroleum).

Figure 1:
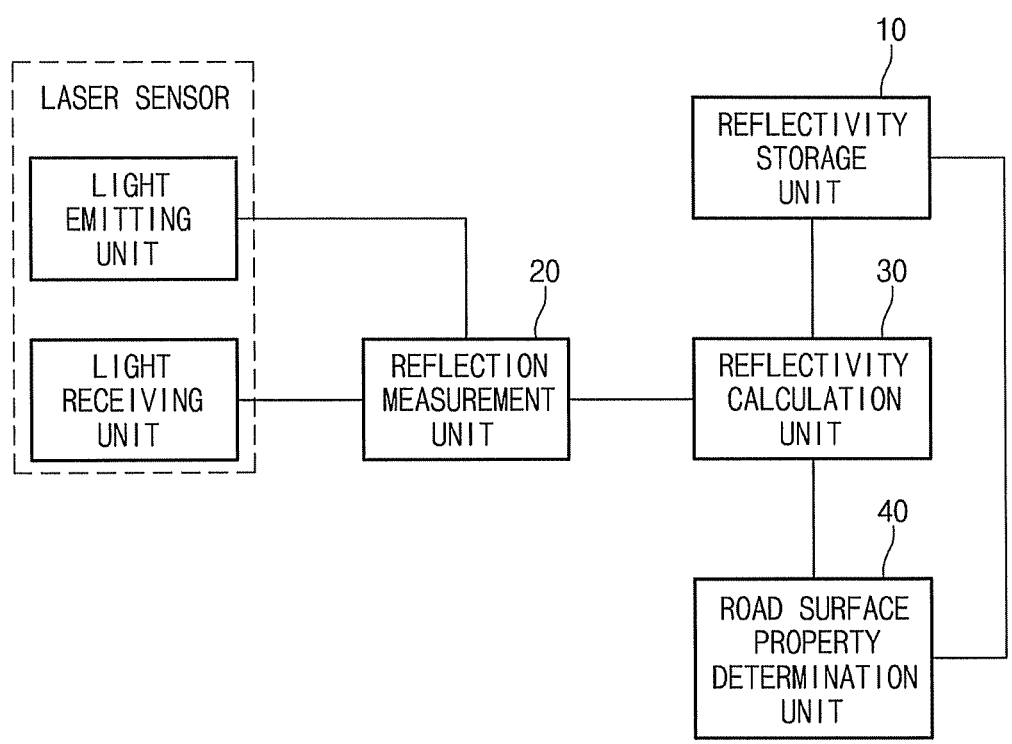
FIG. 1 is a schematic diagram illustrating an exemplary embodiment of an apparatus for detecting a road surface property according to the present invention.

FIG. 1 is a schematic diagram illustrating an exemplary embodiment of an apparatus for detecting at least one road surface property according to the present invention. Although a laser sensor is described in FIG. 1 as an example, it should be noted that various sensors using light such as an infrared sensor may be used.

As shown in FIG. 1, a road surface property detection apparatus according to the present invention includes a reflectivity storage unit 10, a reflection measurement unit 20, a reflectivity calculation unit 30, and a road surface property determination unit 40.

Each element will be described in detail. First, the reflectivity storage unit 10 (such as a memory, flash drive, hard drive, etc) stores a degree of reflectivity (or albedo) table in which a degree of reflectivity of a rainy road and a degree of reflectivity of a snowy road relative to a reflectivity of a dry road (i.e., a reference reflection) are stored. In other words, the reflectivity storage unit 10 stores the reflectivity (or albedo) table in which the degree of reflectivity of the rainy road and the degree of reflectivity of the snowy road relative to the reference reflectivity, which is set to "1", for example, for a dry road, are stored.

For example, if a reflection of the dry road is 100, a reflection of the rainy road is 50, a reflection of the snowy road is 200, and the reflectivity of the dry road is set to "1," the reflectivity of the rainy road is 0.5 and the reflectivity of the snowy road is 2.

Generally, a laser beam emitted from a light emitting unit of a laser sensor has a decreased intensity when bounced back and returned to the laser sensor due to a divergence characteristic thereof. Here, the light emitting unit emits the laser beam toward a road surface in a direction in which a vehicle travels. In addition, a rate at which the intensity of the laser beam that is reflected and returned is decreased is varied depending on the particular road surface property.

A reflectivity table obtained through experimental data is shown as in Table 1 below.

TABLE 1

| Reflectivity | property of road surface |
| --- | --- |
| 0.1~0.5 | rainy road |
| 1 | dry road |
| 2~3 | snowy road |
| . | . |
| . | . |
| . | . |

Figure 2:
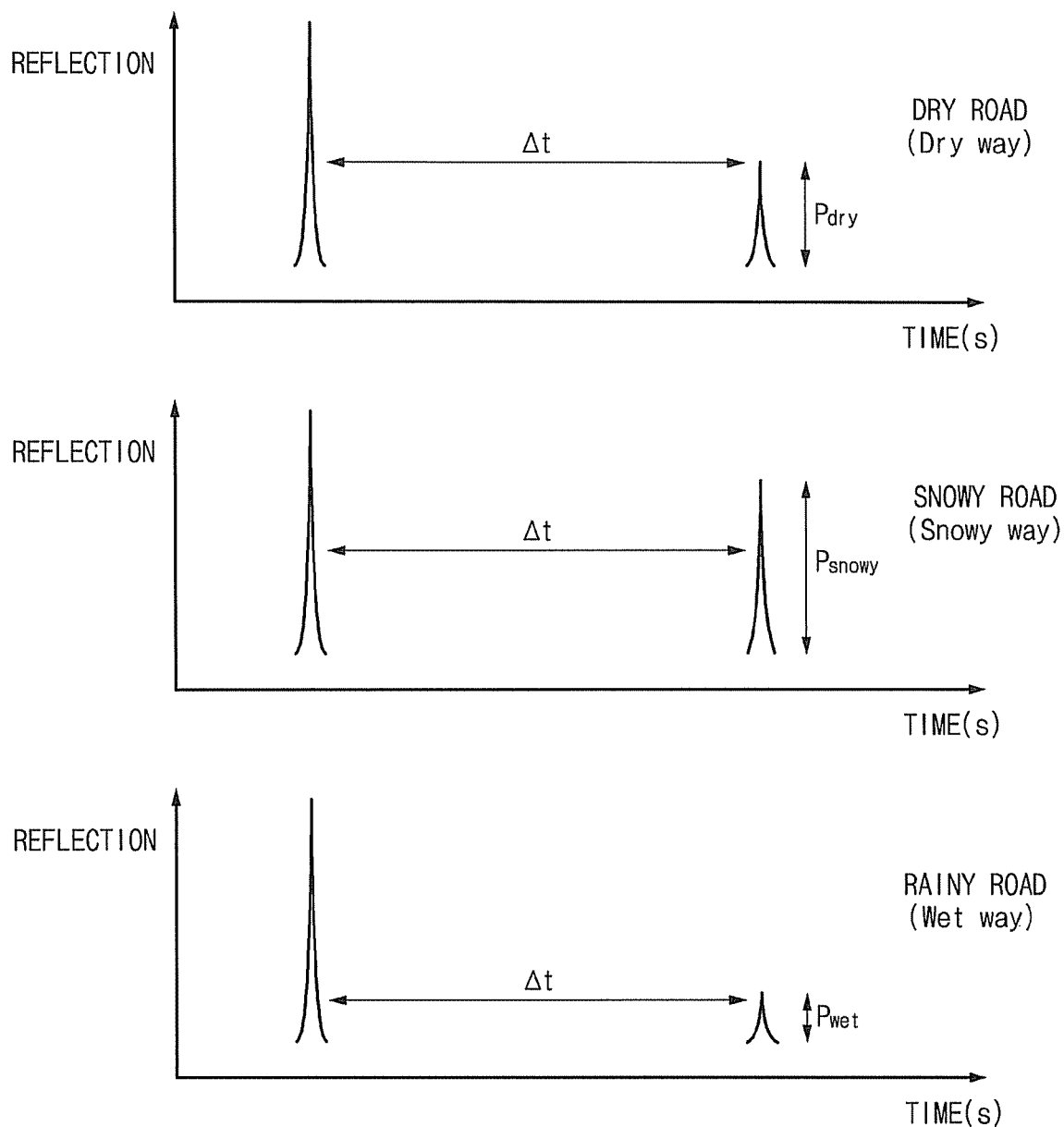
FIG. 2 is a view illustrating an exemplary embodiment of a degree of reflection of rainy and snowy roads according to the present invention.

Table 1 shows the degree of reflectivity of the rainy road and the degree of reflectivity of the snowy road in relation to the reflectivity of the dry road. In other words, Table 1 shows a ratio of the reflection of the rainy road to the reflection of the dry road and a ratio of the reflection of the snowy road to the reflection of the dry road, wherein the reflection of the dry road is set as "1." Here, the reflection indicates the intensity of the laser beam that is reflected and returned. Namely, as shown in FIG. 2, the reflection (or intensity of reflection) of the snowy road is very high compared to that of the dry road, and the reflection of the rainy road is low due to a mirroring effect.

Next, the reflection measurement unit 20 measures the amount of the laser beam, which is emitted through the light emitting unit of the laser sensor, reflected from the road surface, and received by a light receiving unit (hereinafter, "reflection"). The reflectivity calculation unit 30 calculates a ratio of the reflection, measured by the reflection measurement unit 20, in comparison to the reference reflectivity (hereinafter, "reflectivity").

Then, the road surface property determination unit 40 determines a property of the road surface by using a degree of reflectivity calculated by the reflectivity calculation unit 30 based on the reflectivity table stored in the reflectivity storage unit 10. Namely, the road surface property determination unit 40 determines whether the road surface is a snowy road or a rainy road, accordingly.

Additionally, the present invention may further include a road surface property supply unit (not shown) to provide road surface property information determined by the road surface property determination unit 40 to, for example, a system for electronically controlling the operation of the vehicle. Also, a technique for calculating a distance via a laser sensor is a well known technique, and thus, a detailed description thereof will be omitted.

Figure 3:
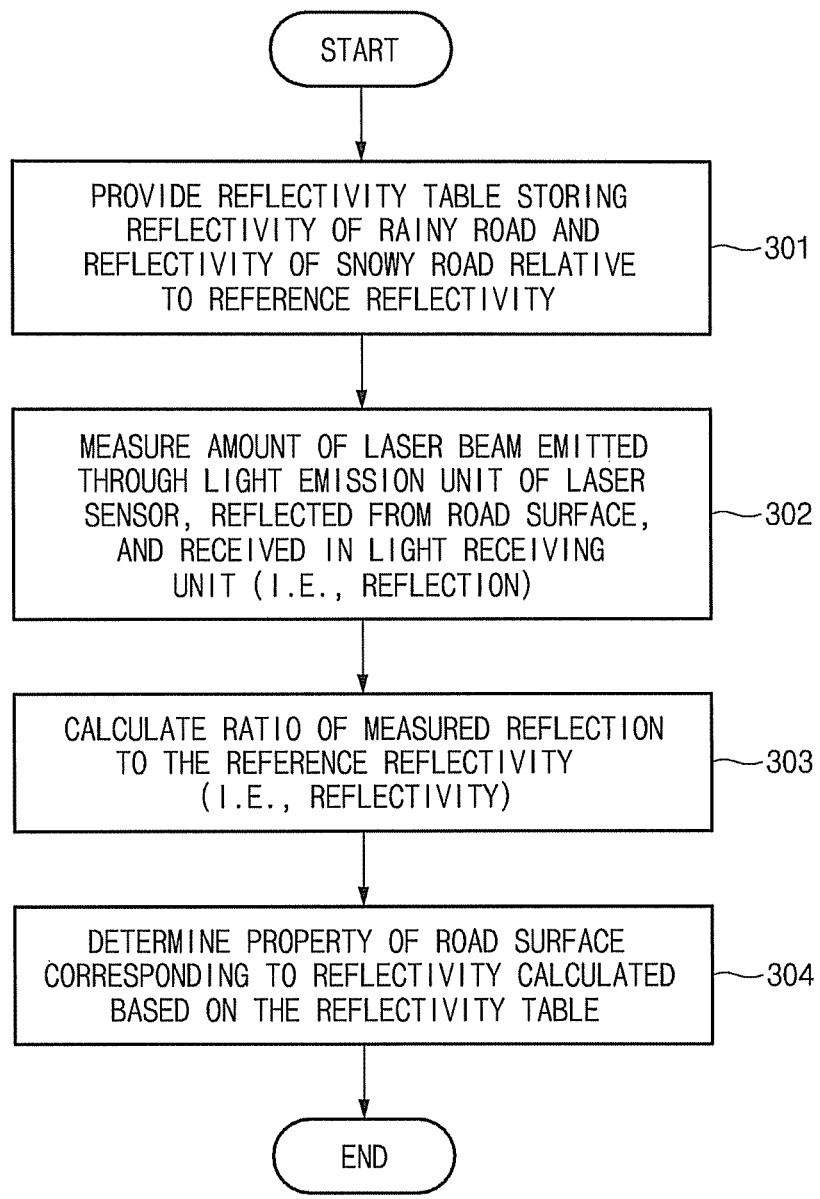
FIG. 3 is a flow chart illustrating an exemplary embodiment of a method of detecting a road surface property according to the present invention.

FIG. 3 is a flow chart illustrating an exemplary embodiment of a method for detecting at least one road surface property according to the present invention. First, the reflectivity storage unit 10 stores the reflectivity table in which the degree of reflectivity of a rainy road and the degree of reflectivity of a snowy road in comparison to the reference reflectivity are stored (301).

Next, the reflection measurement unit 20 measures the amount of the laser beam, which is emitted through the light emission unit of the laser sensor, reflected from the road surface, and received by the light receiving unit (hereinafter, "reflection") (302). The reflectivity calculation unit 30 calculates a ratio of the degree of reflection measured by the reflection measurement unit 20 in comparison with the reference reflectivity (hereinafter, "reflectivity") (303). Subsequently, the road surface property determination unit 40 determines the property of the road surface corresponding to the reflectivity calculated by the reflectivity calculation unit 30 based on the reflectivity table (304). Through this process, the present invention may promptly and accurately determine whether the road surface is that of the rainy road or the snowy road via a single laser sensor.

Figure 4:
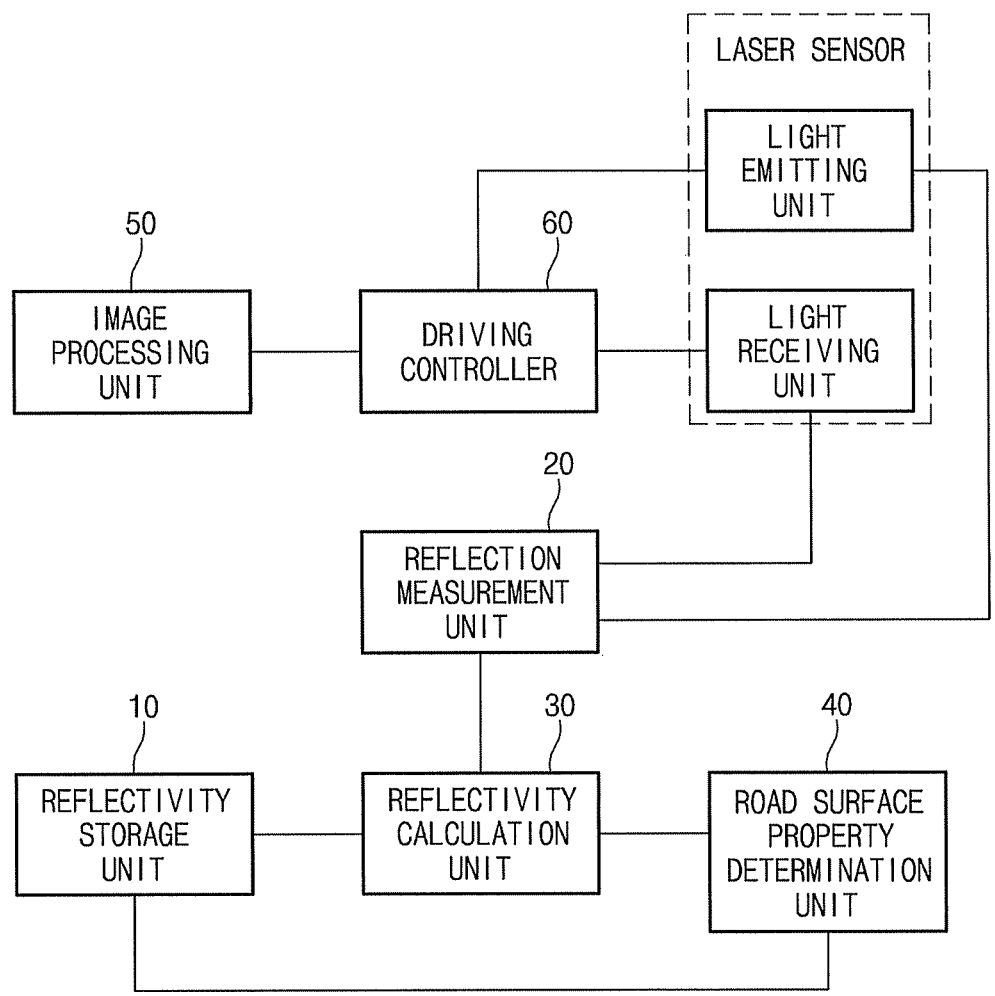
FIG. 4 is a schematic diagram illustrating another exemplary embodiment of an apparatus of detecting a road surface property according to the present invention.

FIG. 4 is a schematic diagram illustrating another exemplary embodiment of an apparatus for detecting a road surface property according to the present invention. Parts that perform similar functions described with respect to FIG. 1 are identified by same reference numerals. As shown in FIG. 4, the road surface property detection apparatus according to the present invention includes the reflectivity storage unit 10, the reflection measurement unit 20, the reflectivity calculation unit 30, the road surface property determination unit 40, an image processing unit 50, and a driving controller 60.

Here, the reflectivity storage unit 10, the reflection measurement unit 20, the reflectivity calculation unit 30, and the road surface property determination unit 40 perform the same functions as described above, and thus a further description thereof will be omitted.

In this embodiment, however, an image processing unit 50 detects abnormalities on the road's surface based on a surface image of the road in front of a vehicle captured by an image capturing device. In other words, by using the image processing unit 50, the laser sensor is not continuously operated but instead operated only in a certain circumstances, thereby increasing its efficiency.

Next, the drive controller 60 operates the laser sensor upon detection of any abnormalities in the road's surface by the image processing unit 50. Thus, the drive controller 60 trigger's of initiates operation of the road surface property detection apparatus upon detection by the image capturing device of an abnormality in the road.

Furthermore, the image processing unit 50 includes a polarization ratio calculator for calculating a polarization ratio image based on a plurality of polarization images, a color characteristic extractor for extracting color characteristic information by using one of the plurality of the polarization images, a texture characteristic extractor for extracting texture characteristic information via one of the plurality of the polarization images, and an abnormality detector for detecting the abnormality of the road surface via the polarization ratio image inputted from the polarization ratio calculator, the texture characteristic information inputted from the texture characteristic extractor, and the color characteristic information inputted from the color characteristic extractor.

Here, the polarization ratio calculator calculates a first polarization image inputted from a first image capturing device and a second polarization image inputted from a second image capturing device in order to calculate the polarization ratio. Here, the polarization ratio obtained by the calculation result is given as a ratio between brightness of the first polarization image and a brightness of the second polarization ratio.

In addition, the first image capturing device and the second image capturing device have a polarization lens mounted thereon at different angles. Therefore, images captured by the first image capturing device and the second image capturing device are images polarized at a predetermined angle.

In general, light reflected by frozen ice or a water film is polarized in a particular direction depending on an angle of reflection. Therefore, when photographing a road that is frozen or has the water film, a vertically polarized image and a horizontally polarized image have a significant difference in brightness.

The color characteristic extractor extracts the color characteristic information by using a polarized image inputted from the second image capturing device. Here, the color characteristic information includes a red (R) image, a green (G) image, a blue (B) image, and intensity thereof. The texture characteristic extractor extracts the texture characteristic information by using a polarized image inputted from the second image capturing device.

Here, texture characteristics are different from color characteristics in that the texture characteristics are not created by a pixel but rather a distribution in proximity. A study of the texture characteristics is conducted in areas of, for example, area division, image classification, or image synthesis depending on the texture characteristic. Particularly, many methods have been suggested in which image classification depending on the texture characteristics is performed until images can be input vividly in a similar scale. To perform the image classification, various methods ranging from using a filter bank to using a structure tenser may be used.

The abnormality detector determines the condition of the road based on a sum of input image information. That is, the abnormality detector detects when the road surface is not normal by using the polarization ratio image inputted from the polarization ratio calculator, the texture characteristic information inputted from the texture characteristic extractor, and the color characteristic information inputted from the color characteristic extractor.

Figure 5:
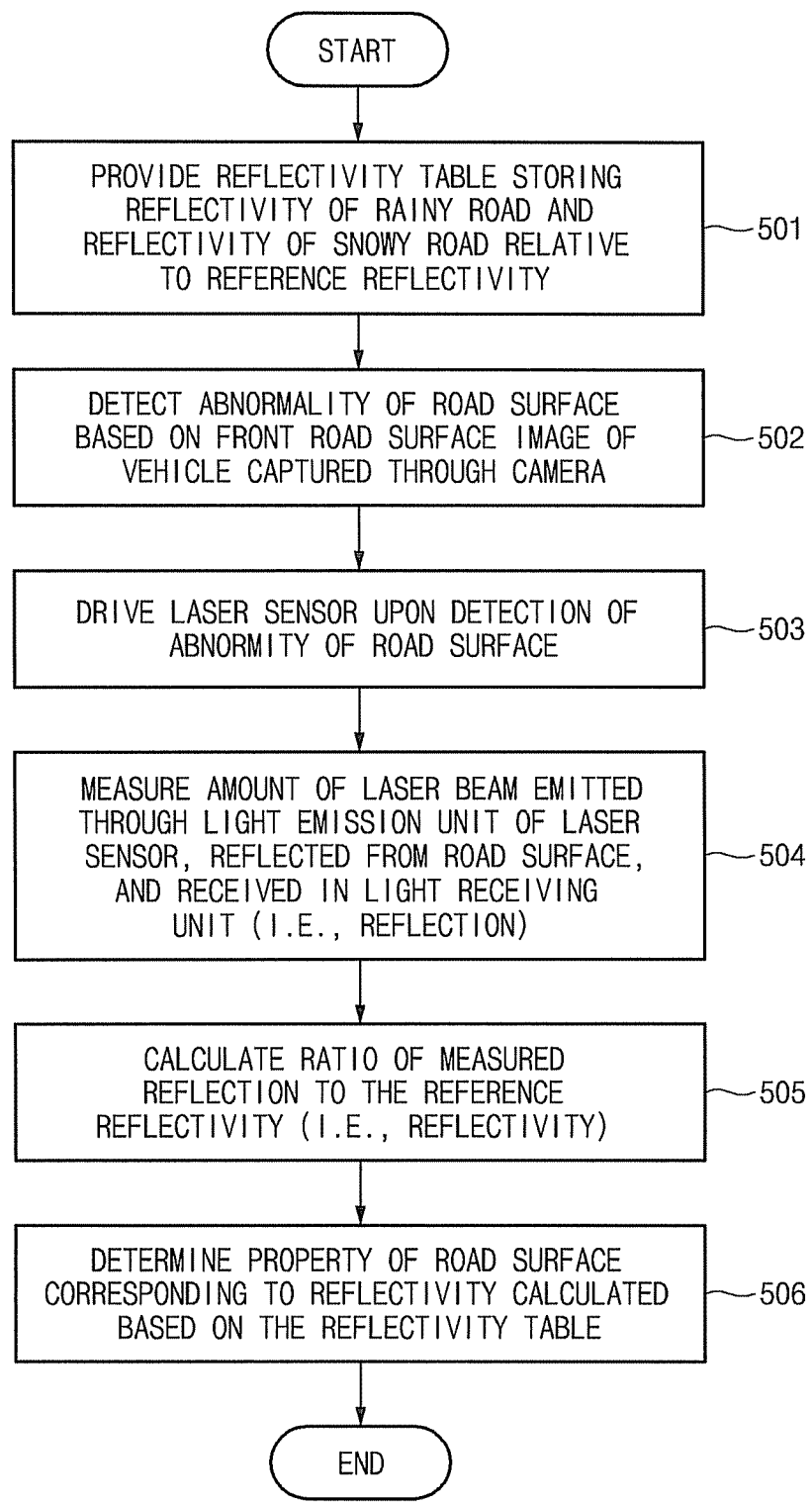
FIG. 5 is a flow chart illustrating another exemplary embodiment of a method of detecting a road surface property according to the present invention.

FIG. 5 is a flow chart illustrating another exemplary embodiment of a method of detecting a road surface property according to the present invention. First, the reflectivity storage unit 10 stores the reflectivity table in which the degree of reflectivity of the rainy road and the degree of reflectivity of the snowy road compared with the reference reflectivity are stored (501). Next, the image processing unit 50 detects abnormalities on the road's surface based on a surface image of the road in front of a vehicle captured via the image capturing device (502). The driving controller 60 then operates the laser sensor upon detection of an abnormity on the road surface via the image processing unit 50 (503). The reflection measurement unit 20 measures the amount of the laser beam, which is emitted through the light emission unit of the laser sensor, reflected from the road surface, and received by the light receiving unit (hereinafter, "reflection") (504).

Next, the reflectivity calculation unit 30 calculates a ratio of the degree of reflection measured by the reflection measurement unit 20 based on the reference reflectivity (hereinafter, "reflectivity") (505). The road surface property determination unit 40 determines whether the degree of reflectivity calculated by the reflectivity calculation unit 30 based on the reflectivity table is that of a snowy road or that of a rainy road (506). Through this process, the present invention may promptly and accurately determine whether the road surface is that of the rainy road or that of the snowy road by using a single sensor.

As described above, according the present invention, the road surface property (e.g., whether the road is wet or icy, that is rainy or snowy respectively) may be detected by measuring a rate at which the laser beam is returned based on a single laser sensor mounted on a front portion of a vehicle so that a need for an additional sensor is removed, resulting in a reduced cost. In addition, the present invention may apply the road surface property obtained without an additional sensor to, for example, a vehicle driving system, thereby promoting driving safety.

Furthermore, the control logic of the present invention may be embodied as non-transitory computer readable media on a computer readable medium containing executable program instructions executed by a processor, controller or the like. Examples of the computer readable mediums include, but are not limited to, ROM, RAM, compact disc (CD)-ROMs, magnetic tapes, floppy disks, flash drives, smart cards and optical data storage devices. The computer readable recording medium can also be distributed in network coupled computer systems so that the computer readable media is stored and executed in a distributed fashion, e.g., by a telematics server or a Controller Area Network (CAN).

In the above, although the embodiments of the present invention have been described with reference to the accompanying drawings, a person skilled in the art should apprehend that the present invention can be embodied in other specific forms without departing from the technical spirit or essential characteristics thereof. Thus, the embodiments described above should be construed as exemplary in every aspect and not limiting.

What is claimed is:

1. An apparatus for detecting a road surface property, the apparatus comprising:
 a memory configured to store a reflectivity table that includes a degree of reflectivity of a rainy road relative to a reference reflectivity, and a degree of reflectivity of a snowy road relative to the reference reflectivity, and a degree of reflectivity of a dry road relative to the reference reflectivity and store a plurality of program instructions;
 a processor configured to execute the program instructions, the program instructions when executed configured to:
 measure a reflection wherein the reflection is an amount of a laser beam that is emitted through a light emitting unit of a laser sensor, reflected from the road surface, and received by a light receiving unit;
 calculate a degree of reflectivity wherein the degree of reflectivity is a measured ratio of the reflection in comparison to the reference reflectivity; and
 detect a road surface property corresponding to the calculated degree of reflectivity based on the reflectivity table;
 wherein the degree of reflectivity of a dry road is 1, the degree of reflectivity of a rainy road is less than 1, and the degree of reflectivity of a snowy road is greater than 1.

2. The apparatus according to claim 1, wherein the program instructions when executed are further configured to:
 provide property information relating to the detected road surface.

3. A method of detecting a road surface property, the method comprising: storing, on a memory, a reflectivity table which includes a degree of reflectivity of a rainy road relative to a reference reflectivity, a degree of reflectivity of a snowy road relative to the reference reflectivity and a degree of reflectivity of a dry road relative to the reference reflectivity;
 measuring, by a controller, a reflection wherein the reflection is amount of a laser beam that is emitted through a light emitting unit of a laser sensor, reflected from the road surface, and received by a light receiving unit;
 calculating, by the controller, a degree of reflectivity, wherein the degree of reflectivity is a ratio of the measured reflection to in comparison to the reference reflectivity; and
 detecting, by the controller, a road surface property corresponding to the calculated degree of reflectivity based on the reflectivity table;
 wherein the degree of reflectivity of a dry road is 1, the degree of reflectivity of a rainy road is less than 1, and the degree of reflectivity of a snowy road is greater than 1.

4. The method according to claim 3, further comprising:
 providing, to by the controller, property information relating the detected road surface.

5. An apparatus for detecting a road surface property, the apparatus comprising:
 a memory configured to store a reflectivity table that includes a degree of reflectivity of a rainy road relative to a reference reflectivity, a degree of reflectivity of a snowy road relative to the reference reflectivity, and a degree of reflectivity of a dry road relative to the reference reflectivity and store a plurality of program instructions;
 and configured to store a plurality of program instructions;
 a processor configured to execute the program instructions, the program instructions when executed configured to:
 detect abnormalities on a road surface based on a surface image of a road in front of a vehicle captured by an image capturing device;
 operate a laser sensor upon detection of an abnormality on the road surface;
 measure a reflection wherein the reflection is an amount of a laser beam that is emitted through a light emitting unit of the laser sensor, reflected from the road surface, and received by a light receiving unit;
 calculate a degree of reflectivity wherein the degree of reflectivity is a ratio of the measured reflection in comparison to the reference reflectivity; and
 detect a road surface property that corresponds to the calculated degree of reflectivity based on the reflectivity table;
 wherein the degree of reflectivity of a dry road is 1, the degree of reflectivity of a rainy road is less than 1, and the degree of reflectivity of a snowy road is greater than 1.

6. The apparatus according to claim 5, wherein the program instructions when executed are further configured to:
 provide property information of relating to the determined road surface.

7. A method of detecting a road surface property, the method comprising:
 Storing, in a memory, a reflectivity table that includes a degree of reflectivity of a rainy road relative to a reference reflectivity, a degree of reflectivity of a snowy road relative to the reference reflectivity, and a degree of reflectivity of a dry road relative to the reference reflectivity;
 detecting, by a controller, abnormalities on the road surface based on a surface image of a road in front of a vehicle captured by an image capturing device;
 operating, by the controller, a laser sensor upon detection of an abnormality of the road surface by the image processing unit;
 measuring, by the controller, a reflection wherein the reflection is an amount of a laser beam that is emitted through a light emitting unit of the laser sensor, reflected from the road surface, and received by a light receiving unit;
 calculating, by the controller, a degree of reflectivity wherein the degree of reflectivity is a ratio of the measured reflection in comparison to the reference reflectivity; and
 detecting, by the controller, the road surface property corresponding to the calculated degree of reflectivity based on the reflectivity table;
 wherein the degree of reflectivity of a dry road is 1, the degree of reflectivity of a rainy road is less than 1, and the degree of reflectivity of a snowy road is greater than 1.

8. The method according to claim 7, further comprising:
providing, to by the controller, property information relating to the determined road surface.

\* \* \* \* \*